United States Patent
Gustafson

(10) Patent No.: US 11,272,920 B2
(45) Date of Patent: Mar. 15, 2022

(54) ONE-WAY ADJUSTABLE LOOP SUTURE CONSTRUCTS AND METHODS OF FORMING AND USING THE SAME

(71) Applicant: Medos International Sàrl, Le Locle (CH)

(72) Inventor: Adam C. Gustafson, Rehoboth, MA (US)

(73) Assignee: Medos International Sarl, Le Locle (CH)

( * ) Notice: Subject to any disclaimer, the term of this patent is extended or adjusted under 35 U.S.C. 154(b) by 115 days.

(21) Appl. No.: 16/583,998

(22) Filed: Sep. 26, 2019

(65) Prior Publication Data

US 2021/0093316 A1 Apr. 1, 2021

(51) Int. Cl.
*A61B 17/04* (2006.01)
*A61F 2/08* (2006.01)

(52) U.S. Cl.
CPC ...... *A61B 17/0485* (2013.01); *A61B 17/0401* (2013.01); *A61F 2/0811* (2013.01); *A61B 2017/0404* (2013.01); *A61B 2017/0409* (2013.01); *A61B 2017/0475* (2013.01); *A61B 2017/0496* (2013.01)

(58) Field of Classification Search
CPC ............ A61B 17/0485; A61B 17/0401; A61B 2017/0404; A61B 2017/0409; A61B 2017/0475; A61B 2017/0496; A61B 2017/0459; A61B 2017/0406; A61B 17/0466; A61B 17/06166; A61B 2017/0414; A61B 2017/0464; A61F 2/0811; A61F 2002/0852; A61F 2002/0882; A61L 17/00
See application file for complete search history.

(56) References Cited

U.S. PATENT DOCUMENTS

| 5,178,629 | A | 1/1993 | Kammerer |
| 7,285,124 | B2 | 10/2007 | Foerster |
| 7,651,509 | B2 | 1/2010 | Bojarski et al. |
| 8,821,544 | B2 | 9/2014 | Sengun et al. |

(Continued)

FOREIGN PATENT DOCUMENTS

| EP | 1 225 948 A1 | 7/2002 |
| EP | 2 581 047 A1 | 4/2013 |

(Continued)

OTHER PUBLICATIONS

European Search Report for Application No. 20198480, dated Feb. 18, 2021 (11 pages).

*Primary Examiner* — Julian W Woo

(57) ABSTRACT

Surgical constructs and methods of use for a one-way adjustable fixation loop are formed by tying two knots in a surgical filament, each knot defining an individual adjustable loop and the individual adjustable loops being interconnected to form the one-way adjustable fixation loop. The knots enable a non-spliceable suture to be used in the creation of the one-way adjustable fixable loop. Embodiments can include a fixation device, such as a cortical button or plate for use in a bone tunnel, and enable the knots to work independent of and suspended below the fixation device. Embodiments can increase the compatibility of the adjustable fixation loop with existing fixation devices and can isolate and protect the knots from damage during use and after implantation.

21 Claims, 13 Drawing Sheets

(56) References Cited

U.S. PATENT DOCUMENTS

| | | | |
|---|---|---|---|
| 8,870,915 B2 | 10/2014 | Mayer et al. | |
| 9,078,651 B2 * | 7/2015 | Astorino | D04G 5/00 |
| 9,301,745 B2 | 4/2016 | Dreyfuss | |
| 9,737,293 B2 | 8/2017 | Sengun et al. | |
| 9,757,113 B2 | 9/2017 | Pasquali et al. | |
| 9,801,625 B2 | 10/2017 | Dooney, Jr. et al. | |
| 9,826,969 B2 | 11/2017 | Larsen | |
| 9,924,939 B1 | 3/2018 | Anderson | |
| 9,974,643 B2 | 5/2018 | Sengun et al. | |
| 10,022,122 B2 | 7/2018 | Singhatat et al. | |
| 10,052,094 B2 | 8/2018 | Spenciner | |
| 10,245,169 B2 * | 4/2019 | Hiernaux | A61B 17/0401 |
| 10,973,507 B2 * | 4/2021 | Stone | A61B 17/0401 |
| 2005/0187577 A1 | 8/2005 | Selvitelli et al. | |
| 2014/0309689 A1 * | 10/2014 | Sikora | A61B 17/683 |
| | | | 606/232 |
| 2018/0085113 A1 | 3/2018 | Michalik et al. | |
| 2018/0221133 A1 | 8/2018 | Lund | |
| 2019/0201185 A1 | 7/2019 | Albertorio et al. | |

FOREIGN PATENT DOCUMENTS

| | | |
|---|---|---|
| EP | 3 463 185 A1 | 4/2019 |
| WO | 2018/169961 A1 | 9/2018 |

* cited by examiner

ONE-WAY ADJUSTABLE LOOP SUTURE CONSTRUCTS AND METHODS OF FORMING AND USING THE SAME

FIELD

The application relates generally to devices and methods for securing soft tissue (e.g., ligament, tendon, graft) to bone, and more particularly to suture constructs that employ particular loop configurations that are adjustable in one direction.

BACKGROUND

Ligaments are the fibrous tissue that connects bones to other bones within the body. Tissue detachment may occur in many ways, e.g., as the result of an accident such as a fall, overexertion during a work-related activity, during the course of an athletic event, or in any one of many other situations and/or activities. These types of injuries are generally the result of excess stress or extraordinary forces being placed upon the tissues. When ligaments are damaged, surgical reconstruction can be necessary, as the ligaments may not regenerate on their own. In the case of a partial detachment, commonly referred to under the general term "sprain," the injury frequently heals without medical intervention, the patient rests, and care is taken not to expose the injury to undue strenuous activities during the healing process. If, however, the ligament or tendon is completely detached from its attachment site on an associated bone or bones, or if it is severed as the result of a traumatic injury, surgical intervention may be necessary to restore full function to the injured joint.

A number of surgical procedures exist for re-attaching ligaments, or other soft tissue, to bone. One example is the knee 100 shown in FIG. 1, which includes anterior and posterior cruciate ligaments 102, 104 extending from the head of the tibia 106 to the intercondylar notch of the femur 108. These ligaments operate to prevent forward and backward relative motion between the two bones. When ruptured (e.g., as can happen in strenuous athletic movements), surgical reconstruction can be necessary.

Tears in the cruciate ligaments of the knee can be repaired using a ligament graft taken from a cadaver (i.e., an allograft) or from a patient's own tissue (i.e., an autograft). Reconstruction procedures generally involve forming a hole in both the femur and tibia, and then securing opposite ends of the ligament graft in these holes. In one cruciate ligament repair procedure, a ligament graft is associated with a surgical implant and secured to the femur. A common femoral fixation means includes an elongate "button," sometimes referred to as a cortical button. The cortical button is attached to a suture loop that is sized to allow an adequate length of the soft tissue graft to lie within the femoral tunnel while providing secure extra-cortical fixation.

Existing devices and methods can be limited because they do not always provide the desired strength or adjustability. In some instances, for example, one or more knots tied to help maintain a location of the suture loop with respect to a cortical button, and thus the graft associated therewith, can loosen or slip. Thus, even if a ligament graft is disposed at a desired location during a procedure, post-operatively the circumference of the loop can increase, causing the graft to move away from the desired location. Further, it can be desirable to limit the number of knots used in conjunction with such devices, because of the potential for the knots loosening and because the additional surface area of the knots can increase the risk of trauma to surrounding tissue. Still further, existing devices and methods also lack adjustability in many instances. For example, in procedures in which multiple ligament grafts are associated with the cortical button, it can be difficult to control placement of one ligament graft without also moving the other ligament graft.

Current adjustable cortical buttons used in orthopedics employing knots are dependent on button geometry and/or multiple loops to achieve security. These are limiting factors for the versatility of the devices and raise potential difficulty in usability. Splices have been used as one-way fixation elements to try and address these concerns, however, such configurations are limited at least because they are not amiable to tape, sutures with tight sheaths and/or cores, and generally require a longer length of the loop to achieve security, thereby increasing the minimum adjustable length. Moreover, in use with purely suspensory fixation devices (e.g., cortical button without locating/retention feature), location or migration of the button with respect to the bone tunnel, possibly caused by offloading of the device due to a non-isometric repair, can cause a reduced interference area on one side of the device, reducing the fixation strength.

Accordingly, there is a need for improved graft fixation devices and methods for use in repair and reconstruction procedures that include, for example, the cruciate ligaments of the knee. In particular, there is a need for devices and methods for positioning and securing ligament grafts that provide increased strength and adjustability without splicing suture or using suture that cannot be spliced.

SUMMARY

The present disclosure is directed to a suture construct that has a one-way adjustable loop. The suture construct can be formed from a single suture filament and, in at least some embodiments, can be coupled to one or more fixation bodies (e.g., cortical buttons) for use in various soft tissue repair procedures. The single suture filament includes at least two knots formed therein, and at least two loop portions. Each loop portion extends from a respective knot, and then the two loop portions are interconnected to form the one-way adjustable loop. They can be interconnected, for example, by passing one loop portion through an opening defined by the other loop portion. Sliding tails formed from the suture filament and extending from the knots can be operable to constrict or otherwise make the loop portions smaller, which in turn constricts or otherwise makes smaller the adjustable loop. Further, constricting tails formed from the suture filament and extending from the knots can be operable to constrict the knots, thereby preventing the sliding tails from sliding with respect to the knots. When the constricting tails constrict the knots, the loop portions, and thus the adjustable loop, cannot be expanded. In at least some embodiments, the constricting tails form a bridge portion that extends between the two knots with the bridge portion keeping the construct in a locked configuration such that the one-way adjustable loop can be constricted but not expanded.

The constructs disclosed herein can be used in various surgical repair procedures in which soft tissue is to be disposed at desired locations with respect to bones. Procedures in which a ligament or graft is designed to be disposed in a bone tunnel can benefit from the presently disclosed constructs and implant devices, such as ACL and MCL repairs. The present disclosure also allows for beneficial use in other types of repairs, including but not limited to AC joint repairs, bunion repairs, and ankle syndesmosis repairs.

In one exemplary embodiment, a suture construct formed from a suture filament includes a first knot formed in the suture filament, a first tail of the suture filament that extends from the first knot, a bride portion of the suture filament, a second knot formed in the suture filament, and a second tail of the suture filament that extends from the second knot. The first knot creates a first loop that extends from the first knot, with the first loop defining a first loop opening. The bridge portion extends from the first knot, connecting the first knot to the second knot. The second knot creates a second loop that extends from the second knot, with the second loop defining a second loop opening, and a portion of the second loop passing through the first loop opening to define an adjustable loop of the suture construct. The adjustable loop defines an adjustable loop opening. The first tail is configured to slide with respect to the first knot to reduce a size of the first loop opening, and thus reduce the size of the adjustable loop opening. Similarly, the second tail is configured to slide with respect to the second knot to reduce a size of the second loop opening, and thus reduce the size of the adjustable loop opening. The bridge portion is configured to prevent expansion of the adjustable loop opening when the suture is manipulated into a locked configuration.

At least one of the first knot or the second knot can be a self-locking knot. Non-limiting examples of such knots include a FIG. 8 noose knot, an expanded FIG. 8 noose knot, and a prusik-style knot. The suture filament can be unspliced at locations of the first and second knots. In some embodiments, a second suture filament can be configured to capture a portion of the knot and/or knots to permit a release of the knot's constriction when traction is applied to the second filament. In one exemplary embodiment of this configuration the second filament is threaded through the first knot and the second knot, with a first limb of the second suture filament extending through the first knot and a second limb of the second suture filament extending through the second knot such that tension on the limbs loosens the respective first and/or second knots.

A fixation body can be coupled to the bridge portion of the suture filament. For example, the bridge portion can be passed through a plurality of through-holes disposed in the fixation body. In some embodiments, a second fixation body can be coupled to the adjustable loop.

The suture can also include an unlocked configuration. In some such embodiments, the suture can be configured to be moved between the unlocked configuration and the unlocked configuration by adjusting relative loading of the bridge portion and/or the tail portion (i.e., the first tail and the second tail). In one exemplary embodiment of a surgical implant, the implant includes a fixation body and a suture filament coupled to the fixation body. The fixation body has a longitudinal axis extending therealong, first and second sides, and first and second through-holes. The suture filament includes a first portion having a first tail, a first knot formed on the first portion, and a first loop portion. The first tail extends through the first through-hole, the first knot is disposed on the first side of the body, and the first loop portion extends from the first knot, away from the body. The suture filament also includes a second portion having a second tail, a second knot formed on the second portion, and a second loop portion. The second tail extends through the second through-hole, the second knot is disposed on the first side of the body, and the second loop portion extends from the second knot, away from the body. The second loop portion is coupled to the first loop portion to define an adjustable loop of the surgical implant. The suture filament further includes a bridge portion that extends from the first knot to the second knot. The first and second knots are configured such that tension on the first tail constricts the adjustable loop by constricting the first loop portion and tension on the second tail constricts the adjustable loop by constricting the second loop portion. The first and second knots are further configured such that tension on the bridge portion prevents expansion of the adjustable loop.

At least one of the first knot or the second knot can be a self-locking knot. Non-limiting examples of such knots include a FIG. 8 noose knot, an expanded FIG. 8 noose knot, and a prusik-style knot. The suture filament can be unspliced at locations of the first and second knots.

In some embodiments, the bridge portion can extend from the first knot, through the first through-hole, across the body, and through the second through-hole to the second knot. The implant can include a second fixation body, in which case the second fixation body can be coupled to the adjustable loop. The fixation body, or bodies, can include a cortical button(s). In some embodiments, the fixation body can include a third through-hole. In some such embodiments, as well as in embodiments that include a second fixation body but do not necessarily include a third through-hole, the surgical implant can include a second suture filament that captures a portion of the first knot and the second knot, with a first limb of the second suture filament extending through the first knot, and a second limb of the second suture filament extending to the second knot. The second suture filament can be configured such that tension on at least one of the first or second limbs loosens the respective first or second knots.

One exemplary method for preparing a surgical implant includes forming a first knot in a first portion of a suture length to form a first tail extending from one side of the first knot and a second portion of the suture length extending from an opposite side of the first knot. The method further includes forming a first loop from the second portion with the first loop being closed by way of the first knot. Still further, a second knot is formed in the second portion of the suture length to form a second tail extending from one side of the second knot and a third portion of the suture length extending from an opposite side of the second knot. The method further includes forming a second loop from the third portion, the second loop being closed by way of the second knot, and the second loop being interconnected with the first loop to define an adjustable fixation loop of the suture construct.

The second portion of the suture length can include a bridge portion that extends between the first knot and the second knot. In some embodiments, at least one of the first tail or the second tail can be configured to constrict a size of an opening defined by the adjustable fixation loop when tension is applied to the tail(s) to constrict a size of first or second openings defined by the respective first or second loops.

The method can also include passing the first tail through a first through-hole of a fixation body, passing the second tail through a second through-hole of the fixation body, and passing the second portion of the suture length through at least two of: (1) the first through-hole of the fixation body; (2) the second through-hole of the fixation body; (3) another through-hole of the fixation body; or (4) still another through-hole of the fixation body. Still further, the method can include coupling the adjustable fixation loop to a second fixation body.

BRIEF DESCRIPTION OF DRAWINGS

This disclosure will be more fully understood from the following detailed description taken in conjunction with the accompanying drawings, in which.

DETAILED DESCRIPTION

Figure 1:
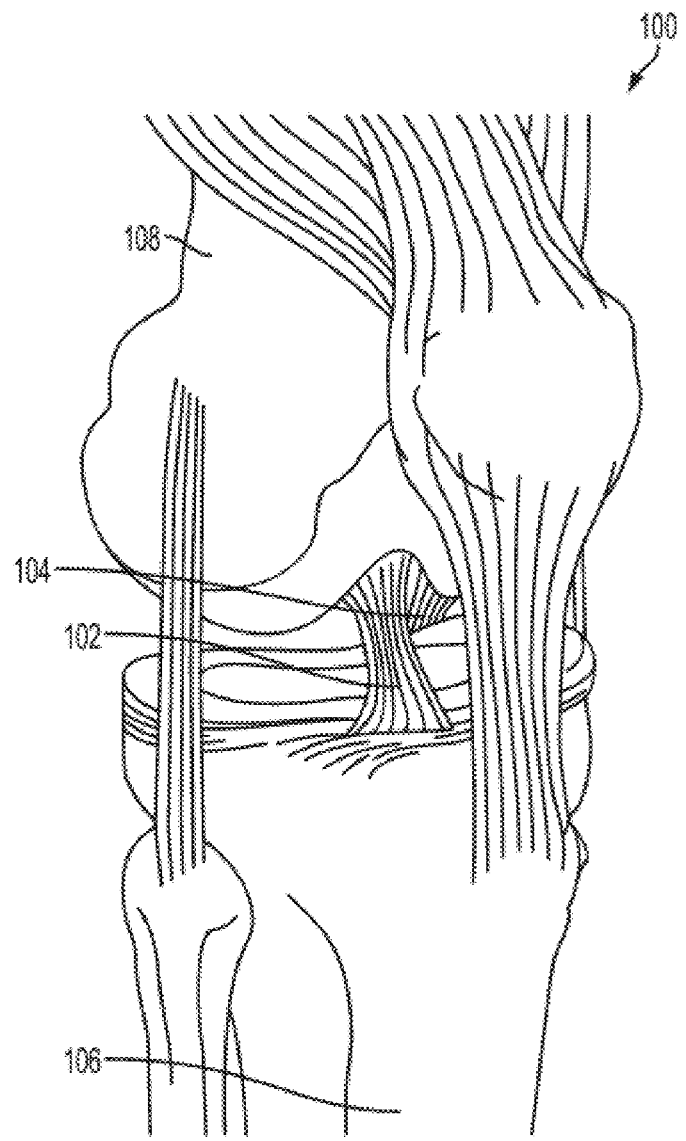
FIG. 1 is a schematic side view of the anatomy of a human knee.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present disclosure is defined solely by the claims. The features illustrated or described in connection with one exemplary embodiment may be combined with the features of other embodiments. Such modifications and variations are intended to be included within the scope of the present disclosure. Further, in the present disclosure, like-numbered components of the embodiments generally have similar features. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

The figures provided herein are not necessarily to scale. Further, to the extent arrows are used to describe a direction a component can be tensioned or pulled, these arrows are illustrative and in no way limit the direction the respective component can be tensioned or pulled. A person skilled in the art will recognize other ways and directions for creating the desired tension or movement. Likewise, while in some embodiments movement of one component is described with respect to another, a person skilled in the art will recognize that other movements are possible. Additionally, a number of terms may be used throughout the disclosure interchangeably but will be understood by a person skilled in the art. By way of non-limiting example, the terms "suture," "filament," and "suture filament" may be used interchangeably.

The present disclosure is generally directed to methods and devices for securing soft tissue, including but not limited to ligaments, tendons, and grafts, to bone or other desired locations within a subject (e.g., human, animal). Surgical implants described herein generally include a body or fixation body, such as a "cortical button," and a suture construct formed from a suture (also referred to as a filament or suture filament) threaded through, or otherwise associated with, the body in a manner that provides a one-way adjustable loop. The one-way adjustable loop can be formed by two interconnecting loops of suture (see, e.g., loop portions 501, 503 of FIGS. 2 and 4). The size of the one-way adjustable loop can be adjusted by manipulating one or both of the interconnecting loops of suture using terminal ends of the suture. In use, a graft, and/or other tissue (e.g., ligament(s), tendon(s)), can be coupled to or otherwise associated with the one-way adjustable loop, for instance by placing the tissue through an opening defined by the one-way adjustable loop, with the one-way adjustable loop extending from a fixation body of an implant. The tissue can be securely positioned within a bone tunnel by placing and securing the fixation body outside of the tunnel and securing the position of the one-way adjustable loop after it has been adjusted to a desired size, and thus desired location, to maintain a location of the graft with respect to the bone tunnel.

Figure 2:
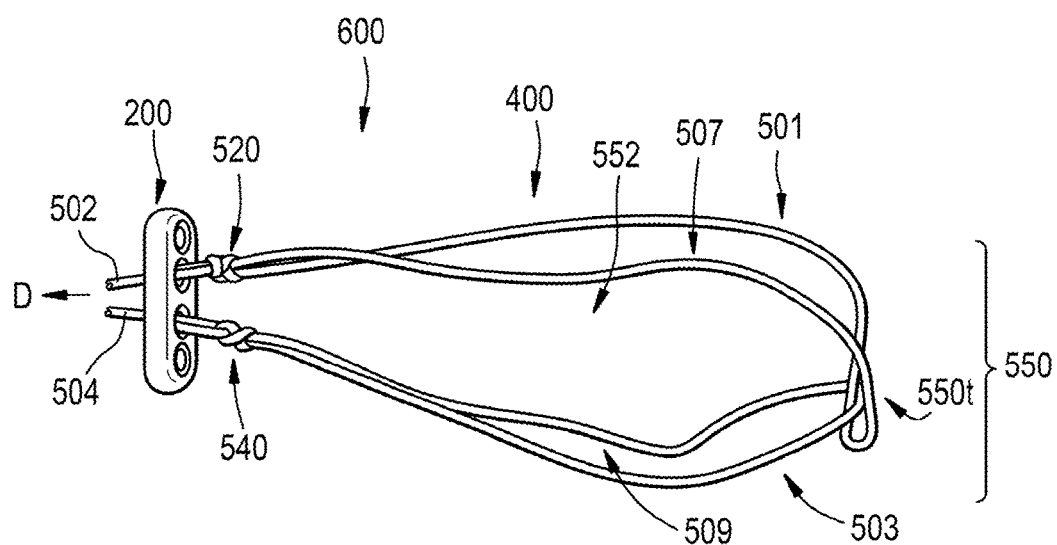
FIG. 2 is a side view of one exemplary embodiment of an adjustable fixation implant.

FIG. 2 is an illustration of one exemplary repair implant 600 that includes a surgical construct 400 coupled to or otherwise associated with a fixation body, as shown a cortical button 200. The surgical construct includes a one-way adjustable loop 550 that can be formed by two loop portions 501, 503 interconnected with each other. The implant 600 is arranged with a first tail 502 of the surgical construct 400 passing through a second through-hole 212 of the body 200 (see FIG. 3 to better see the second through-hole 212) and a second tail 504 passing through a first through-hole 210 of the body 200 (see FIG. 3 to better see the first through-hole 210). The tails 502, 504 extend from knots 520, 540 formed on the surgical construct 400, with the knots 520, 540 being disposed on a same side of the body 200 as the one-way adjustable fixation loop 550. The knots 520, 540 and/or the through-holes 212, 210 can be sized in a manner such that the knots 520, 540 cannot easily pass through the through holes 212, 210. Additionally, a bridge portion 505 (see FIGS. 4A and 4B) can extend between the first and second knots 520, 540. For example, in conjunction with the implant as illustrated in FIG. 2, a bridge portion 505 can extend from the first knot 520, though the second through-hole 212, across an opposite face of the body 200 (as compared to the one-way adjustable fixation loop 550), though the first through hole 210, and to the second knot 540. Alternatively, and more akin to the illustration of the suture construct 400 provided in FIGS. 4A and 4B, the bridge portion 505 can extend directly between the two knots 520, 540 without passing through, over, across, and/or in contact with the body 200. The fixation loop 550 is considered a one-way loop because a force applied to the loop 550, such as by applying it to the body 200, to expand the one-way adjustable fixation loop 550 is resisted by the bridge 550, constricting the knots 520, 540 and preventing the tails 502, 504 from sliding.

In the configuration illustrated in FIG. 2, tension on either of the first or second tails 502, 504, such as being applied by a force in a direction D on either or both of the tails 502, 504, can reduce a size of openings 507, 509 defined by the loop portions 501, 503 associated with the respective tails 502, 504 and knots 520, 540. As the size of the openings 507 and/or 509 reduce, so too does a size of an opening 552 defined by the one-way adjustable fixation loop 550. More particularly, as one or both of the openings 507, 509 constricts, a terminal end 550t of the loop 550 moves towards the body 200, the terminal end 550t being at a location approximately where the two loop portions 501, 503 of filament are engaged with each other. A person skilled in the art will recognize that the filament may move such that the terminal end 550t is not necessarily at a location where the two loops 501, 503 of filament are engaged. For example, if one loop portion 507, 509 is significantly larger than the other, the terminal end 550t may not be the location at which the loop portions 507, 509 are engaged with each other. Thus, the terminal end 550t of the loop 550 can more generally be a portion of the loop 550 that is approximately furthest away from the body 200, and in at least some instances it can be the location at which the loop portions 507, 509 are interconnected.

Further, the configuration illustrated in FIG. 2 is configured such that tension or force applied to the body 200, and/or to the adjustable fixation loop 550, in an attempt to expand the adjustable fixation loop 550 can be prevented because such applied tension or force can cause tension on the bridge portion 505, which in turn can constrict or lock the two knots 520, 540. The foregoing notwithstanding, the present disclosure contemplates the ability to "unlock" the knots 520, 540 such that the constriction of the loop 550 can, optionally, be reversed, as described in greater detail below.

In operation, the tails 502, 504 of the suture 500 may be pulled on together or in alternating fashion to reduce the length of the adjustable fixation loop 550 as desired. After a desired location of the adjustable fixation loop 550 is achieved, a force can be applied to the adjustable fixation loop 550 to create tension and cause the knots 520, 540 to constrict against the slidable portion of the suture 500 (e.g., the suture tails 502, 504 passing through their respective knots 520, 540), thus maintaining the length of the adjustable fixation loop 550.

The knots 520, 540 knots in the construction of the loop 550 allow for non-spliceable suture 500 to be used in the creation of the one-way adjustable fixation loop 550. Even if the suture 500 is spliceable, the construct 400 configuration can be such that no splices are used, at least with respect to where the knots 520, 540 are located. The use of knots as opposed to splices provides enhanced security and greater versatility for manufacturing a one-way constricting loop because it allows for the use of sutures that are not compatible with alternative locking mechanisms, such as splices, among other benefits. Accordingly, the knots 520, 540 provided for herein can be described as being unspliced since they do not contain splices as previously used in medical applications. The implant 600, and the other disclosed configurations, or components thereof (e.g., various configurations of suture constructs), allow the knots 520, 540 to work independent of the body 200 (e.g., a primary fixation device, cortical button, anchor, or plate). This arrangement increases the compatibility of the adjustable fixation loop 550 to be used in conjunction with many different types of fixation devices, as well as helping to isolate and/or protect the knots 520, 540 when a user trims the tails 502, 504 due, at least in part, to the knots 520 being disposed on one side of the body 200 and the tails 502, 504 on the other side of the body 200. Further, the use of knots 520, 540 as opposed to splices provides for a construct 400 that has a shorter locking mechanism. Typical splices are about 17 millimeters in length, as opposed to the knots 520, 540, which are approximately in the range of about 2 millimeters per knot to about 3 millimeters per knot. The reduced length of the knots takes up less loop length, and thus provides for greater adjustability in use.

In the illustrated embodiment the surgical construct 400 is formed from a single filament. A person skilled in the art will understand the disclosures provided for herein can be adapted for formation using multiple filaments though. For example, in some instances, a bridge portion akin to the bridge portion 505 can be formed by tying or otherwise connecting two separate filaments together, each filament having one knot, one looped portion, and one sliding tail, akin to the knots 520, 540, looped portions 501, 503, and sliding tails 502, 504, formed therein. The use of a single filament can provide benefits in ease of manufacturing and/or formation, strength, and reliability, among others. Notably, to the extent any illustrations herein appear to show different colored or shaded filaments, such differences exist to accentuate the differences between the portions of the filament being used for the various features (e.g., tail, loop portion, etc.); the illustrated embodiments are each formed from a single filament.

Figure 3:
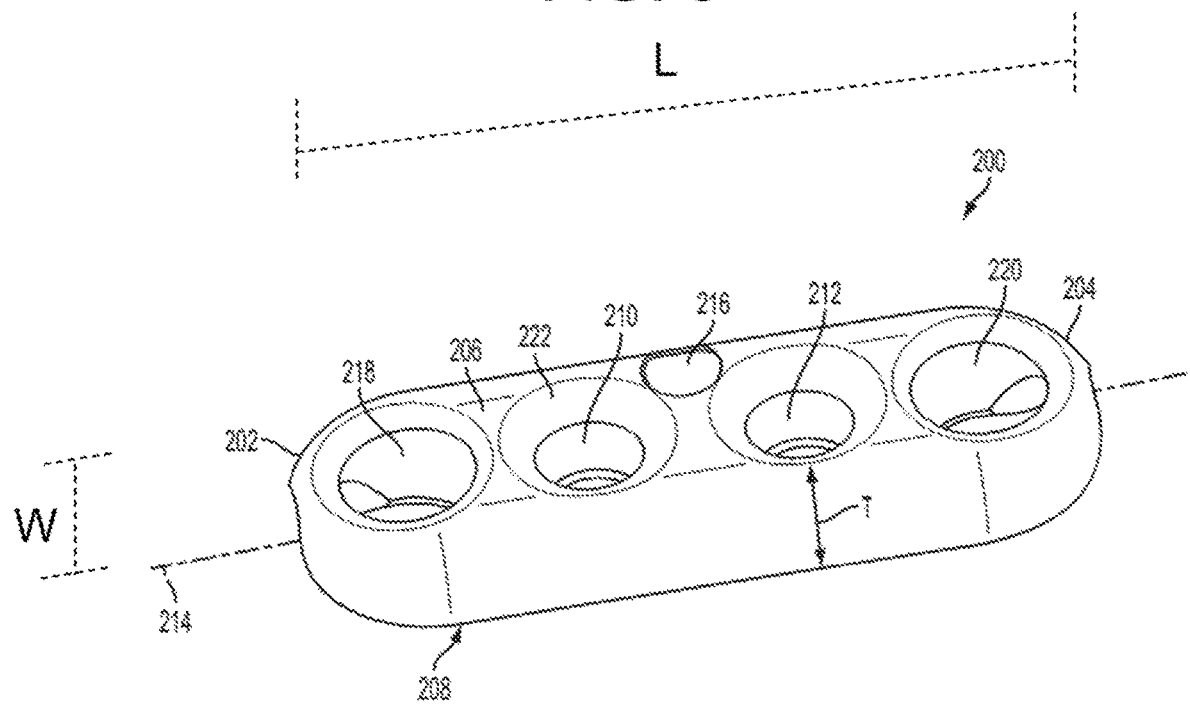
FIG. 3 is a perspective view of a fixation body of the adjustable fixation implant of FIG. 2.

FIG. 3 illustrates one embodiment of a body 200 for used in conjunction with the suture constructs provided for in the present disclosure. The body, also known as a "cortical button," 200 can have an elongate, somewhat rectangular shape with rounded or curved terminal ends 202, 204. A plurality of through-holes can be formed in the body extending between a first side 206 and a second, opposing side 208. A first through-hole 210 and a second through-hole 212 can be adjacent to one another and positioned such that their centers lie along a longitudinal axis 214 of the body 200. A third through-hole 216 can be positioned between the first through-hole 210 and the second through-hole 212, and its center can be offset by a distance from the longitudinal axis 214, as shown in the figures. The body 200 can also include fourth and fifth through-holes 218, 220 positioned outside the first and second through-holes 210, 212 near the terminal ends 202, 204 of the body. These through-holes can also be centered along the longitudinal axis 214.

As shown, the first through fourth through-holes 210, 212, 218, 220 can have diameters that are substantially the same, and a space separating the adjacent through-holes can be substantially the same for each adjacent pair. A length L of the body 200 can be defined by a distance between the terminal ends 202, 204 and a width W can be defined by a distance between first and second sidewalls of the body 200 extending along the first or second surfaces 206, 208. The body 200 can also have a thickness T defined by a distance between the first and second surfaces 206, 208, as shown in FIG. 3.

In some embodiments, the length L of the body 200 can be in a range of about 5 mm to about 20 mm, the width W can be in a range of about 2 mm to about 6 mm, and the thickness T can be in a range of about 1 mm to about 3 mm. In one exemplary embodiment, the length L can be about 12 mm, the width W can be about 4.25 mm, and the thickness T can be about 2 mm.

Diameters of the through-holes 210, 212, 216, 218, 220 can be in a range of about 1 mm to about 2 mm. The diameters of the first and second through-holes 210, 212 can be selected such that a knot formed from a suture length is unable to pass through the hole. Further, in some embodiments the third through-hole 216 can be smaller than the first and second through-holes 210, 212. For example, in one embodiment the diameters of the first, second, fourth, and fifth through-holes 210, 212, 218, 220 can be about 1.6 mm, and the diameter of the third through-hole 216 can be about 1.2 mm.

The body 200 can include one or more features that allow easier manipulation of suture lengths threaded therethrough. For example, a top edge 222 or a bottom edge 224 of any of the through holes 210, 212, 216, 218, 220 can be chamfered or rounded so as to ease threading of a suture length therethrough and reduce the possibility of damage to a suture length from contact with a sharp-edged corner. In addition, one or more cut-outs can be provided on the second surface 208 of the body 200 to facilitate pulling a suture length through one of the plurality of through-holes when the second surface 208 is, for example, pressed against the outer surface of a bone.

In some embodiments the body 200 can include recesses on the second surface 208 to receive the knots 520, 540 of the construct 400 when the body 200 is pressed against a surface, such as a bone. Such a configuration can prevent the knots 520, 540 from interfering with contact between the second surface 208 and the surface of the bone, or at least minimizing the impact of the knots 520, 540 on such contact.

The body 200 illustrated in FIG. 3 is merely one example of a body according to the teachings provided herein. A body configured to be associated with a suture length to create a surgical implant as described herein can have a variety of different shapes, sizes, and features, and can be made of a variety of different materials. These various shapes, sizes, and materials can depend, at least in part, on characteristics of other components with which the body is used, such as the suture length, the soft tissue graft type, etc. The shape, size, and material can also depend on the particular type of procedure being used to implant the body. Thus, while in the illustrated embodiment the body 200 is somewhat rectangular having curved terminal ends 202, 204, in other embodiments the body can be substantially tubular or have any of a variety of other shapes. Configurations beyond cortical buttons are also possible, and thus the term "body" is by no means limited to just include cortical buttons. Various anchors, plates, and other fixation devices known to those skilled in the art can be used in conjunction with the suture constructs (e.g., construct 400) provided for herein, or otherwise derivable from the present disclosures, to form adjustable fixation implants like the implant 600.

Additionally, the placement of the plurality of through-holes formed through the body 200 can be varied as well. For example, in the illustrated embodiment the longitudinal axis 214 is shown as a central longitudinal axis of the body. However, in other embodiments the axis 214 may be offset toward one side of the body. The plurality of through-holes can similarly be offset, or can be angled with respect to the body 200. Further, the first and second through-holes 210, 212 need not necessarily be centered along the same axis as the fourth and fifth through-holes 218, 220. In some instances, fewer or more through-holes can be used. For example, in some instances, the third through-hole 216 may be omitted. In instances in which the third through-hole 216 is used, however, typically the center of the third through-hole 216 should be offset from whatever axis is defined by the centers of the first and second through-holes 210, 212.

The descriptions and illustration of an implantable body provided in conjunction with FIG. 3 are merely examples of surgical implants for securing soft tissue to bone that can be used in conjunction with the suture constructs provided for herein (e.g., the suture construct 400). Non-limiting examples of surgical implants, as well as methods, for securing soft tissue to bone, are further provided below, as well in U.S. Pat. Nos. 9,974,643 and 9,757,113, the contents of each which is hereby incorporated by reference in their entireties. More particularly, the techniques for performing the procedures, and the types of implant bodies disclosed therein, can be used in conjunction with the suture constructs, and related techniques, disclosed herein.

Figure 4A:
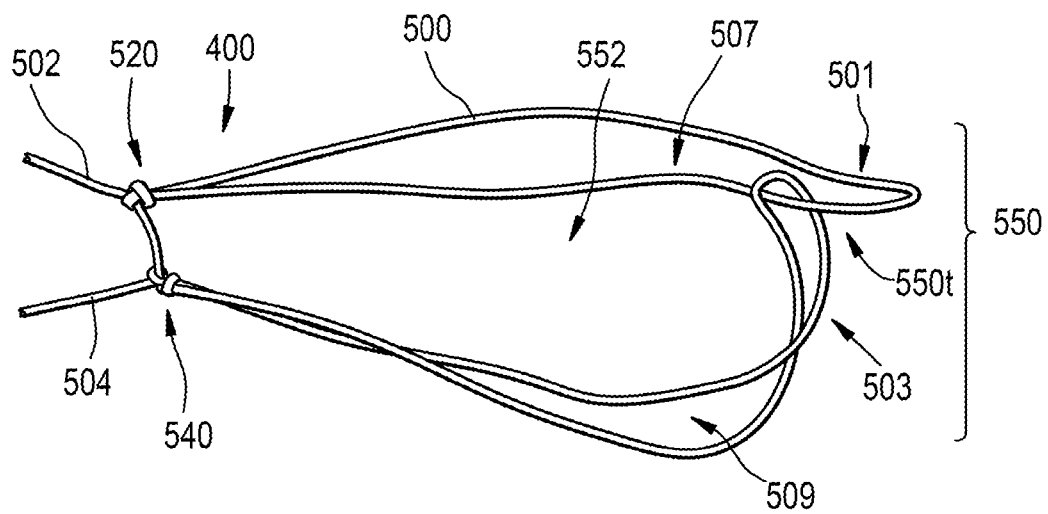
FIG. 4A is a side view of a suture construct of the adjustable fixation implant of FIG. 2, the suture construct having a one-way adjustable loop.
Figure 4B:
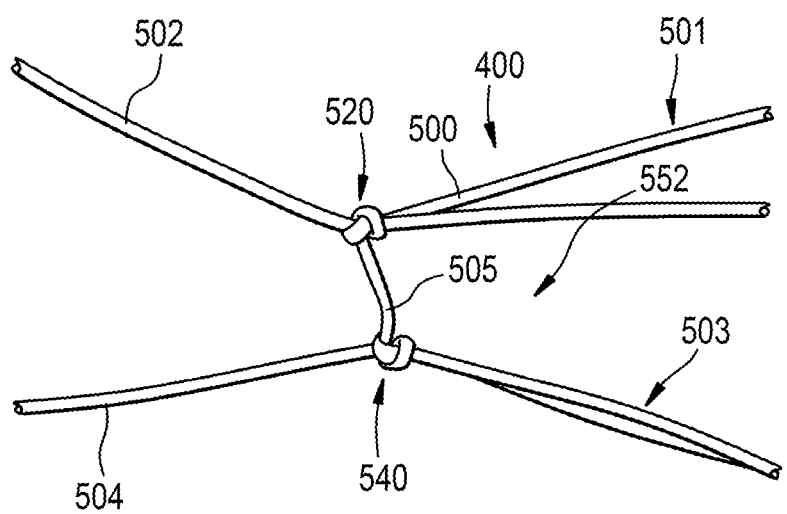
FIG. 4B is a detailed side view of a portion of the suture construct of FIG. 4A that includes two FIG. 8 noose knots.

FIGS. 4A and 4B illustrate the surgical construct 400 of the implant 600, the construct 400 including the one-way adjustable loop 550 constructed using two FIG. 8 noose knots 520, 540. As shown, the surgical construct 400 can be made from a single length of suture 500 with the first tail 502 extending from the first knot 520 and the second tail 540 extending from the second knot 540. The knots 520, 540 can be tied in two sections of the suture 500 such that extending from opposed or opposite sides of the knot are tails 502, 504 and adjustable loop portions, or loops, 501, 503, the loop portions defining the openings 507, 509. The loops 501, 503 can be closed loops, defined by the respective knots 520, 540. As shown, ends of the loop portions 501, 503 (illustrated at the terminal end 550t) can be linked to form the one-way adjustable fixation loop 550, which itself defines the opening 552. In the illustrated embodiment, the loop portions 501, 503 are linked by passing the filament 500 from one loop portion (e.g., the loop portion 503) through an opening (e.g., the opening 507) defined by the filament 500 from the other loop portion (e.g., the loop portion 501). As a result, each loop portion 501, 503 passes through the respective openings 507, 509 defined by the filament 500 of the other loop portion 501, 503. Other ways of linking one loop portion to the other may also be possible provided that such configurations allow the filament 500 of the loop portions 501 and/or 503 to advance towards the knots 520

540 (and/or a fixation body when the construct 400 is used in conjunction with a fixation body) to decrease the size of the opening 552 defined by the one-way adjustable fixation loop 550. In operation, tension on either of the first and second tails 502, 504 can cause reduction in the corresponding openings 507, 509 of the first and second adjustable loop portions 501, 503, which in turn can reduce a size of the opening 552 defined by the one-way adjustable fixation loop 550.

The knots 520, 540 can be formed on the filament 500 in many different manners. In the illustrated embodiment, shown in greater detail in FIG. 4B, the knots 520, 540 are formed as FIG. 8 noose knots. More generally, the knots 520, 540 can most aptly be classified as a type of running knot and/or single strand single loop slipknots. These knots, when arranged as in the one-way surgical construct 400, can exhibit a self-locking behavior due to, for example, a majority of tension applied to 552 being directed to the knots 520, 540 opposed to the tails 502, 504 on which they are running. The illustrated embodiments provide some exemplary self-locking knots that allow for the knots to be used in a one-way configuration while still having the ability to be reversed if desired, including the FIG. 8 noose knot (see FIGS. 4A-7B), the extended FIG. 8 noose knot (see FIGS. 8A and 8B), and prusik-style knots (see FIGS. 9 A and 9B). The illustrated embodiments are by no means limiting on the type and/or number of knots that can be used as knots (e.g., knots 520, 540) in conjunction with the suture constructs (e.g., the construct 400) provided for herein to achieve the desired functionality of the constructs. A person skilled in the art, in view of the present disclosures, will recognize other knots that are suitable for use in conjunction with the constructs and implants of the present disclosure. Further, the bridge portion 505 connects the first knot 520 to the second knot 540 and tension on the bridge portion 505 can constrict the knots 520, 540 and prevent expansion of the one-way adjustable fixation loop 550.

Manipulation of the single filament 500 to form each of the tails 502, 504, the loop portions 501, 503, the knots 520, 540, and bridge portion 505 can be achieved in a variety of manners. The order by which the various features (e.g., tails, loop portions, knots, bridge portion, etc.) of the construct 400 are formed is not typically critical. As generally shown, the single filament 500 includes two terminal ends, which end up being the tails 502, 504. In one exemplary embodiment, the filament 500 extends from the tail 502, is formed into the first loop 501, and is tied around tail 502 to form the knot 520 and opening 507. The filament 500 can exit to the first knot 520 and can be tied into knot 540 forming bridge 505. The working end of the filament 500 can be threaded through opening 507 and a bend can be made around loop 501 to form loop 503. The working end can be returned and passed through knot 540 to form opening 509 and tail 504.

In some embodiments, and as shown in FIGS. 10A-10C and 11, soft tissue may be hung through the one-way adjustable fixation loop 550, thereby coupling the soft tissue to the loop 550, and more broadly a repair implant (e.g., the implant 600). Any number of techniques can be used to associate soft tissue with the loop 550, creating a coupled configuration in which movement of the loop 550 results in movement of the soft tissue. In some embodiments, the one-way adjustable fixation loop 550 can be suspended from a primary fixation device, such as the cortical button 200 or plate, by the bridge portion 505 of the suture 500 between the two knots 520, 540. In other embodiments, as described in greater detail below, the construct 400 can be operated by itself, without any fixation devices coupled to it. In still other embodiments, as also described in greater detail below, the construct 400 can be operated with a plurality (i.e., two or more) fixation devices. One example of such a configuration is provided for in FIG. 5.

Figure 5:
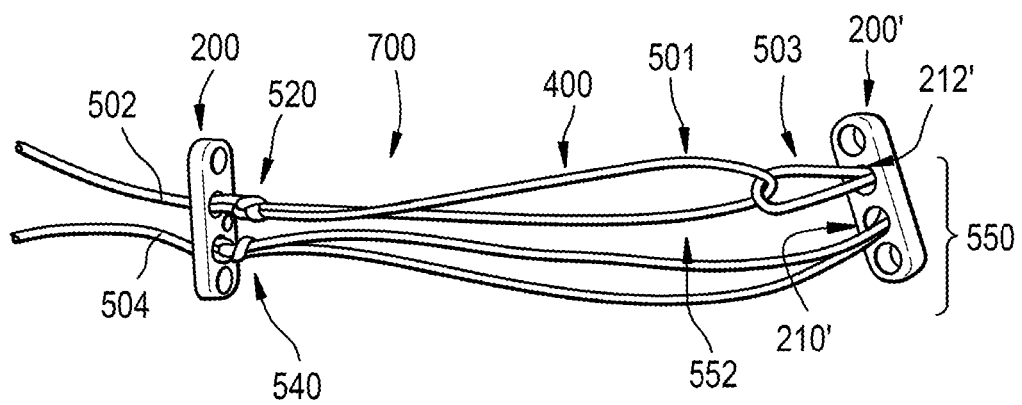
FIG. 5 is a side view of the adjustable fixation implant of FIG. 2 having a second fixation body coupled to the suture construct, the suture construct being further illustrated in FIG. 4A.

FIG. 5 is an illustration of one embodiment of a surgical implant 700 including the suture 500 having the one-way adjustable loop 550 formed by the two loop portions 501, 503 and knots 520, 540, as well as two cortical buttons 200, 200'. The second body 200' can be threaded onto or otherwise associated with the adjustable fixation loop 550 using techniques known to those skilled in the art for associating a fixation body with suture. In the illustrated embodiment, the loop portion 503 is threaded through one through-hole 210' of the body 200' and back through a second through-hole 212' of the body 200'. The second body 200' can be used in a variety of contexts, including but not limited to pull two sides of a bone, or two separate bones, together, by selectively applying tension to one or both of the tails 502, 504. Further, additional non-limiting examples of implant configurations utilizing multiple fixation bodies are described below with respect to FIGS. 12A-12C.

The construct 400 itself can be used without fixation bodies to achieve similar functions, such as drawing two bones together. More generally, the construct 400 can be used with other components of a body beyond bones (e.g., tissue), and even in contexts outside of a surgical procedure, and thus with one or more objects. Some non-limiting examples of the types of procedures that can benefit from using a plurality of fixation bodies in conjunction with the constructs (e.g., the construct 400) disclosed herein can include AC joint repairs, bunion repairs, and ankle syndesmosis repairs. Although discussion herein primarily focuses on use in the medical field, a person skilled in the art will appreciate that the suture constructs provided for herein can have applications in many fields and industries as they can generally be used to advance one or more objects towards a fixed location and/or advance one or more objects towards another object(s).

Figure 6:
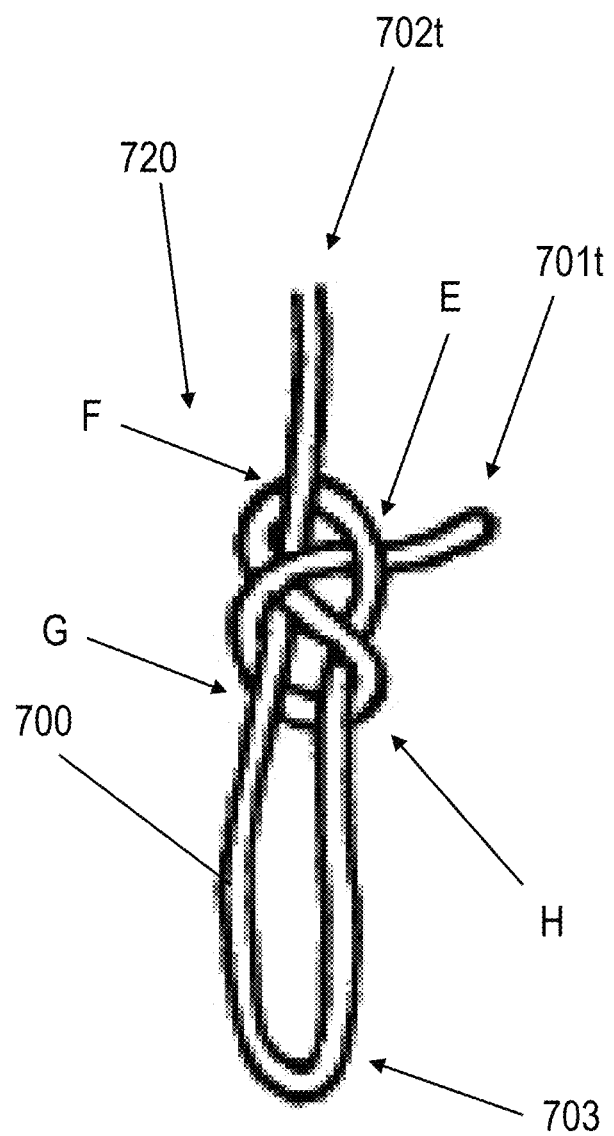
FIG. 6 is a schematic side view of one exemplary embodiment of forming a FIG. 8 noose knot.

FIG. 6 illustrates one exemplary embodiment for forming a FIG. 8 noose knot from a suture 700. As shown, the suture 700 includes a terminal end 701t. The suture 700 is formed into a FIG. 8 configuration 708, with the terminal end 701t extending through a top half 708a of the FIG. 8 as it completes the FIG. 8 shape, as shown at a location E. The suture 700 can pass through the top half 720a of the FIG. 8 at least once, as shown at a location F, and through a bottom half of the FIG. 8 at least twice, as shown at locations G and H. In the context of the constructs provided for herein, the portion of the suture 700 that is on an opposite end of the suture as the terminal end 702t, identified in FIG. 6 as portion 701t, can be used to form the remaining portions of a suture construct (e.g., the construct 400) in accordance with the present disclosures, and thus does not typically represent an opposed terminal end of the suture 700. Further, in the context of the constructs provided for herein, the portion of the filament 700 identified as 703 can be a loop portion and the terminal end 702t can be a tail.

Figure 7A:
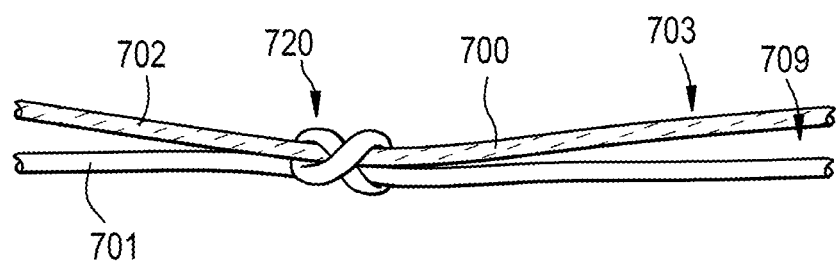
FIG. 7A is a detailed side view of a portion of a suture construct similar to the suture construct of FIG. 4A, the suture construct including the FIG. 8 noose knot of FIG. 6 disposed in an adjusting orientation.
Figure 7B:
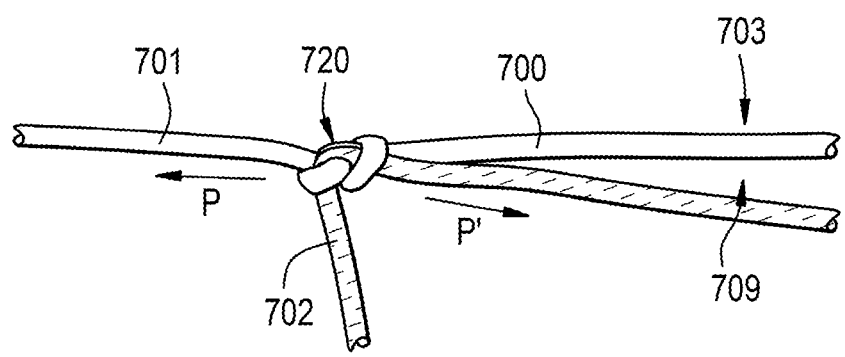
FIG. 7B is a detailed side view of the portion of the suture construct of FIG. 7A disposed in a locking orientation.

FIG. 7A shows the suture 700 tied with the FIG. 8 noose knot 720 of FIG. 6 to form the loop portion 703, a sliding tail or post 702 (associated with portion 702t of FIG. 6), and a constricting tail 701 (associated with the terminal end 701t of FIG. 6). In operation, the sliding tail 702 is free to be pulled through the FIG. 8 noose knot 720 to constrict the loop portion 703, i.e., it causes an opening 709 defined by the loop portion 703 to get smaller. As described above, such movement can likewise cause an opening defined by the loop portion 703 and an inter-connected loop portion (not illustrated) to also get smaller. By applying tension on the constricting tail 701, as shown in FIG. 7B, the suture 700 can be placed in a locked configuration. More particularly, opposing tension can be applied to the constricting tail 701 and the loop 703 by applying forces in directions P and P', respectively, the forces constricting the knot 720 such that the tail 702 kinks substantially perpendicular to the direction the tail 702 naturally exits the knot 720 and/or substantially perpendicular to the force applied to the loop portion, causing the knot to constrict or lock, thus preventing further movement of the sliding tail 702 through the FIG. 8 noose knot 720. A person skilled in the art will recognize the force applied to the constricting tail 701 to place the knot 720, or more generally a suture construct that includes the knot 720, in a locked configuration does not necessarily have to be in a direction that is substantially perpendicular to the direction the tail 701 naturally exits the knot 720 and/or substantially perpendicular to the sliding tail 702, and that there are other ways by which the knot 720 can be placed in a locked configuration.

Figure 8A:
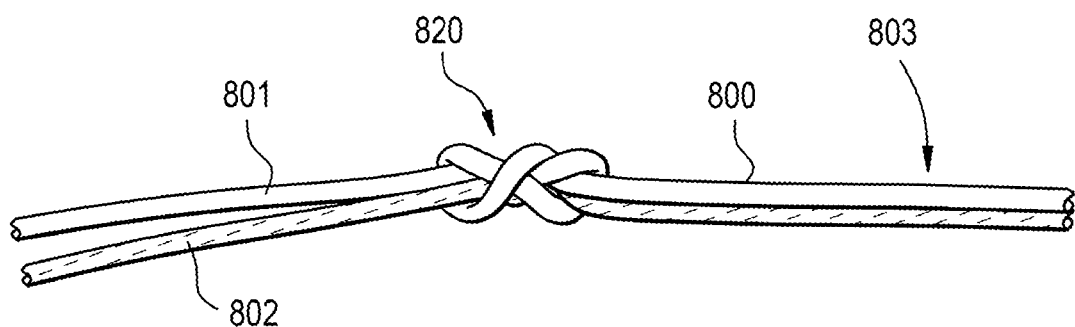
FIG. 8A is a detailed side view of a portion of a suture construct similar to the suture construct of FIG. 4A, the suture construct including an extended FIG. 8 noose knot in an adjusting orientation.
Figure 8B:
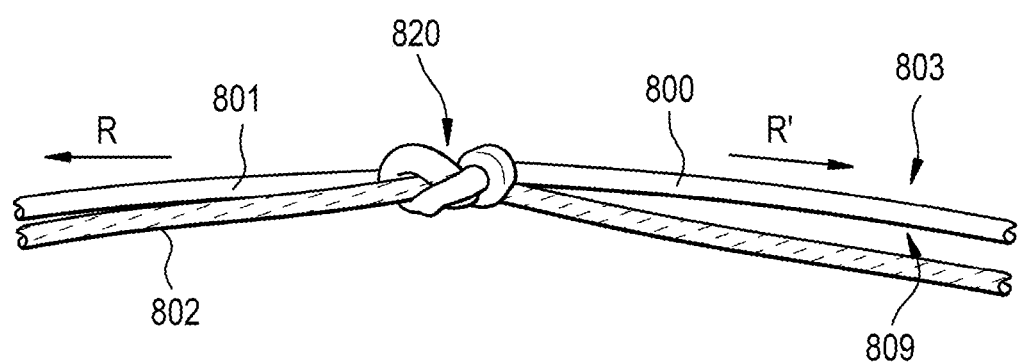
FIG. 8B is a detailed side view of the portion of the suture construct of FIG. 8A disposed in a locking orientation.

FIG. 8A shows a suture 800 tied with an extended FIG. 8 noose knot 820 to form a loop portion 803, a constricting tail or post 801, and a sliding tail or post 802. In operation, the sliding tail 802 is free to be pulled through the FIG. 8 noose knot 820 to constrict the loop portion 803, i.e., it causes an opening 809 (FIG. 8B) defined by the loop portion 803 to get smaller. As described above, such movement can likewise cause an opening defined by the loop portion 803 and an inter-connected loop portion (not illustrated) to also get smaller. By applying tension on the constricting tail 801, as shown in FIG. 8B, the suture 800 can be placed in a locked configuration. More particularly, tension can be applied to the constricting tail 801 and loop 803 by applying opposing tensile forces in directions R and R', respectively, to cause the knot 820 to constrict or lock, thus preventing further movement of the sliding tail 802 through the extended FIG. 8 noose knot 820. A person skilled in the art will recognize the force applied to the constricting tail 801 to place the knot 820, or more generally a suture construct that includes the knot 820, in a locked configuration does not necessarily have to be in the direction(s) R and R', and that there are other ways by which the knot 720 can be placed in a locked configuration. Compared with the FIG. 8 noose knot 720, the extended FIG. 8 noose knot 820 reduces bending of the slidable tail 802. Similar to the FIG. 8 noose knot 720, the constricting tail 801 can become part of a bridge portion, and the knot 820 can also be reversible such that the sliding tail 801 can be moved again.

Figure 9A:
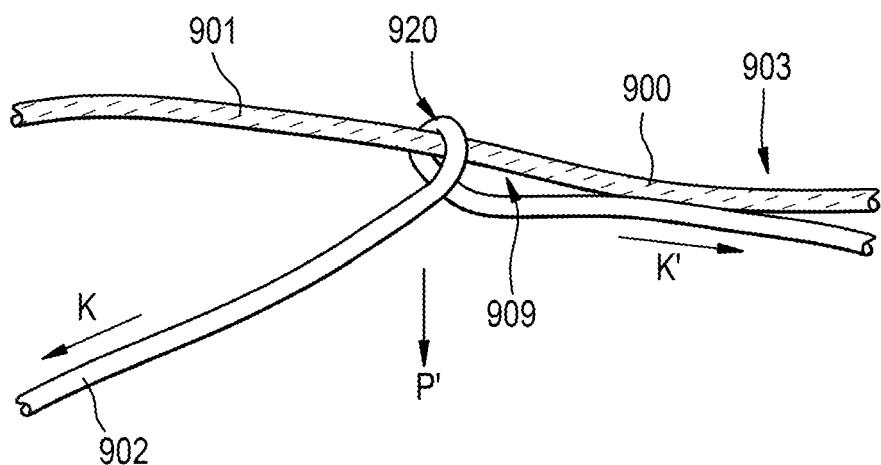
FIG. 9A is a detailed side view of a portion of a suture construct similar to the suture construct of FIG. 4A, the suture constructing including a single prusik style knot.

FIG. 9A shows a suture 900 tied with a prusik-style knot 920 to form a loop portion 903, a constricting tail 902, and a sliding tail or post 901. The prusik-style knot 920 can be created, for example, by piercing the end of the suture 900 through a central portion of the suture 900. In operation, the sliding tail 901 is free to be pulled through the prusik-style knot 920 to constrict the loop portion 903, i.e., it causes an opening 909 defined by the loop portion 903 to get smaller. As described above, such movement can likewise cause an opening defined by the loop portion 903 and an inter-connected loop portion (not illustrated in FIG. 9A) to also get smaller. By applying tension on the constricting tail 902 and loop 903, the suture 900 can be placed in a locked configuration. More particularly, opposing tension can be applied to the constricting tail 902 and loop 903 by applying forces in directions K and K' to cause the knot 920 to constrict or lock, thus preventing further movement of the sliding tail 901 through the prusik-style knot 920. A person skilled in the art will recognize the force applied to the constricting tail 902 to place the knot 920, or more generally a suture construct that includes the knot 920, in a locked configuration does not necessarily have to be in the direction as exemplified but, generally, simply develop tension in the constricting portion of the knot 920. A person skilled in the art will further recognize that there are other ways by which the knot 920 can be placed in a locked configuration. Similar to the knots 720 and 820, the tail 902 can become part of a bridge portion, and the knot 920 can also be reversible such that the sliding tail 901 can be moved again and/or the loop portion 903 can be expanded.

Figure 9B:
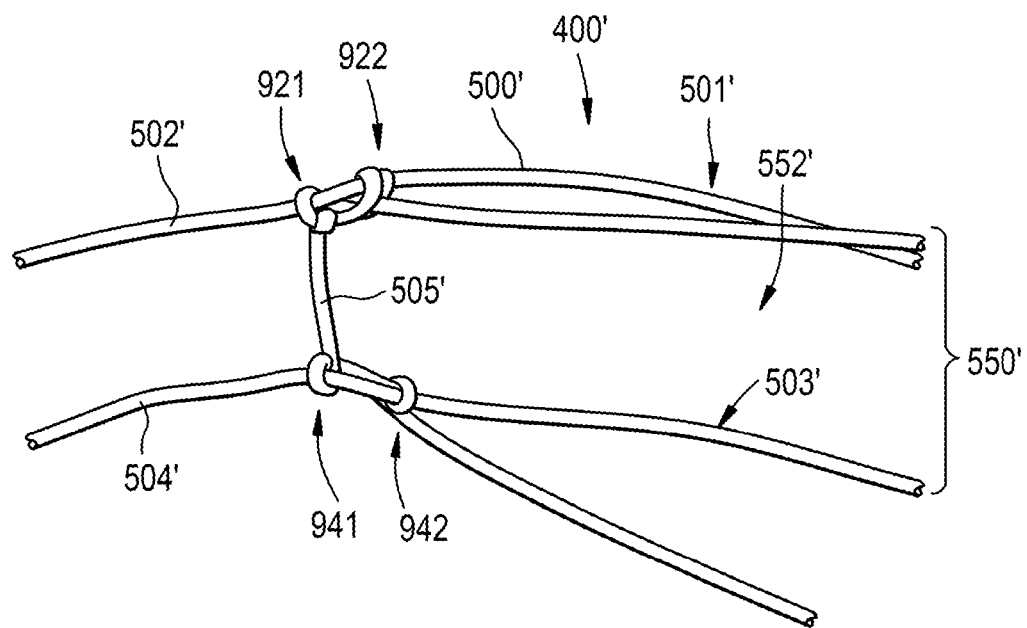
FIG. 9B is a detailed side view of one exemplary embodiment of a suture construct similar to the suture construct of FIG. 4A, the suture construct including a one-way adjustable loop constructed using at least two prusik style knots (as shown, four such knots)

The prusik-style knot 920 may be stacked in series to increase security as needed, and FIG. 9B shows a surgical construct 400' that includes two prusik-style knots 921, 922 forming a first loop portion 501' of an adjustable fixation loop 550' defining an opening 552', and two prusik-style knots 941, 942 forming a second loop portion 503' of the adjustable fixation loop 550'. Comparing FIG. 9A to 9B, the equivalent of the constricting tail 902 can form a bridge portion 505', the equivalent of the sliding tail 901 can form first and second tails 502', 504', and the equivalent of the loop portion 902 can form first and second loop portions 501', 503'. When used with a cortical button (not shown), for example, such as a free-floating cortical button, the increased cross-sectional area created by the knots 921, 922, 941, 942 suspended below the button can act as a locating mechanism within a bone tunnel, more closely constraining the location of the button with respect to a tunnel aperture of the tunnel. This can help to center the body about the tunnel and reduce the likelihood of compromised fixation of the primary fixation compared to solutions where the suture below the button is straight. In fact, any of the configurations provided for herein can allow the knots (e.g., the knots 520, 540, 720, 820) to be used as a locating mechanism.

Just as in FIG. 9B, in which the equivalent of the tails 901, 902 of the prusik-style knot 920 can be used to form the first and second tails 502', 504' and the bridge portion 505', respectively, and the equivalent of the loop portion 903 can be used to form the first and second loop portions 501', 503', when a FIG. 8 noose knot 720 or an extended FIG. 8 noose knot 820 is used in the surgical construct 400, the tails 502, 504 of the surgical construct 400 can be the sliding tails 702, 802, the loop portion 501, 503 of the surgical construct 400 can be the loop portions 703, 803, and the bridge portion 505 of the surgical construct 400 can be the constricting tails 701, 801.

Further, the present disclosure allows for the tails 702, 802, 901 to be moved back to a configuration more akin with that illustrated in FIGS. 7A, 8A, and 9A, respectively, to remove the knots 720, 820, 920 from the locked configuration, thus allowing the sliding tails 702, 802, 901 to be moved again. When the constricting tail 701, 801, 902 is in an unlocked configuration, tension can be applied to the loop portion 703, 803, 903 to allow the opening 709, 809, 909 defined by the loop portion 703, 803, 903 to be expanded.

Figure 10A:
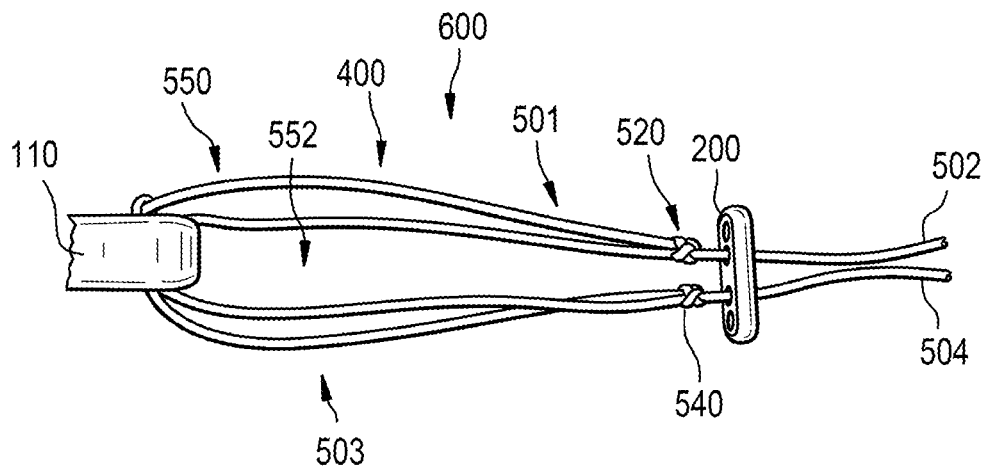
FIGS. 10A-10C are schematic side views of steps of one exemplary embodiment of a method for tightening a one-way adjustable loop.
Figure 10B:
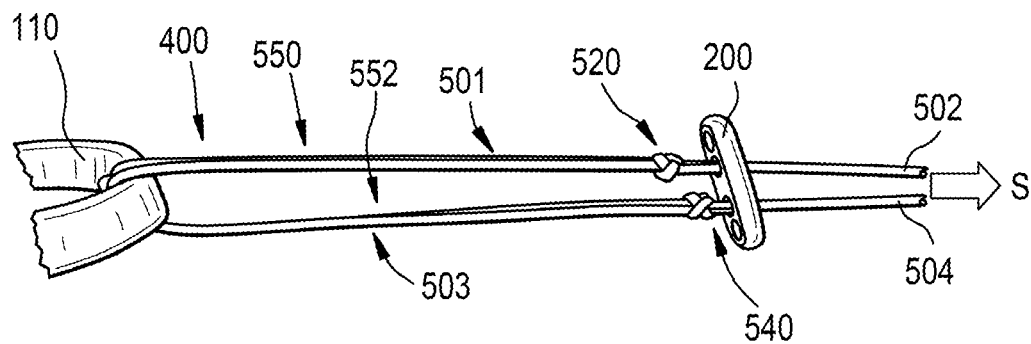
Figure 10C:
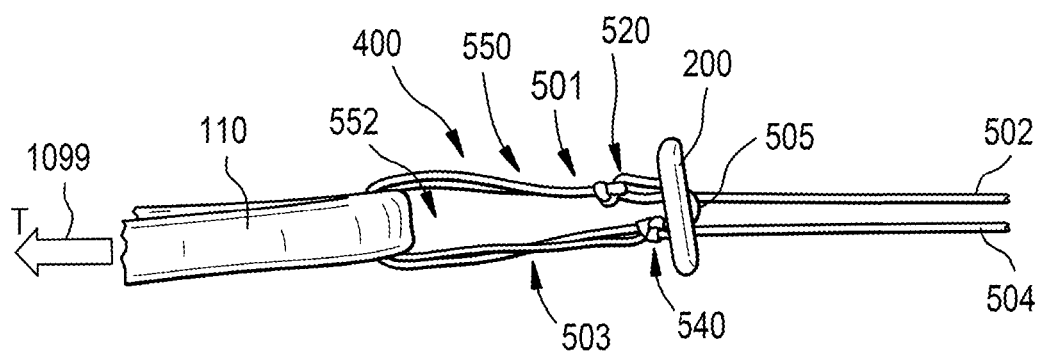

FIGS. 10A-10C are illustrations of steps for tightening the loop of one exemplary embodiment of a one-way adjustable loop. FIG. 10A shows the implant 600 that includes the surgical construct 400 and the body 200 with a soft tissue 110 coupled to the adjustable fixation loop 550. The adjustable fixation loop is formed by the loop portions 501 and 503. FIG. 10B illustrates a tightening or constricting operation where a force applied in a direction S to either or both of the first and second tails 502, 504 of the surgical construct 400 constricts the adjustable fixation loop 550, decreasing a size of the opening 552 and drawing the soft tissue 110 towards the body 200, to a position shown in FIG. 10C.

More particularly, tension applied to the tail 502 can constrict the loop portion 501, and tension applied to the tail 504 can constrict the loop portion 503. In FIG. 10C, a force applied in a direction T to the soft tissue 110 does not result in the adjustable fixation loop 550 expanding because the resulting tension causes the bridge portion 505 of the surgical construct 400 to constrict the knots 520, 540, meaning the knots 520, 540 are in a locked configuration. As described elsewhere herein, the knots 520, 540 can be moved to an unlocked configuration, in which case a force applied in the direction T, as well as other forces applied to the loop 550, can cause such expansion.

The use of the knots 520, 540 permits greater versatility for manufacturability of the one-way constricting loop constructs 400 by enabling the use of sutures 500 that are not compatible with alternative locking mechanisms (e.g., splices). One such example is sutures with solid cores, such as DePuy Synthes Dynacord™ suture, available from DePuy Synthes Sports Medicine (Mitek) of Raynham, Mass. Dynacord™ suture is constructed with a solid core which is essential for the suture's ability to contract when hydrated. Additional information about such suture configurations is provided at least in U.S. Pat. No. 8,870,915 to Mayer et al., the contents of which is incorporated by reference herein in its entirety. The contraction behavior of the constructs provided for herein (e.g., the construct 400) may be used in conjunction with the Dynacord technology to resist losses of the repair due to creep, reapproximate tissue between which a gap has formed or maintain a compressive force on approximated tissue. The presence of a solid core and its required intimate relationship with the sutures braid appeal for locking mechanisms such as knots that are external to the suture's core.

The tightening steps described above, for instance in conjunction with FIGS. 10A-10C, can also be used in conjunction with surgical procedures. The surgical constructs and implants provided herein can be used in a variety of procedures to secure a soft tissue graft to bone. One common procedure is the repair of a torn or ruptured ACL in a patient's knee. An exemplary repair procedure can include forming a bone tunnel through a patient's tibia 106 and femur 108 (see FIG. 1) in a manner known in the art. This can produce, for example, the bone tunnel 130 illustrated in FIG. 11.

Figure 11:
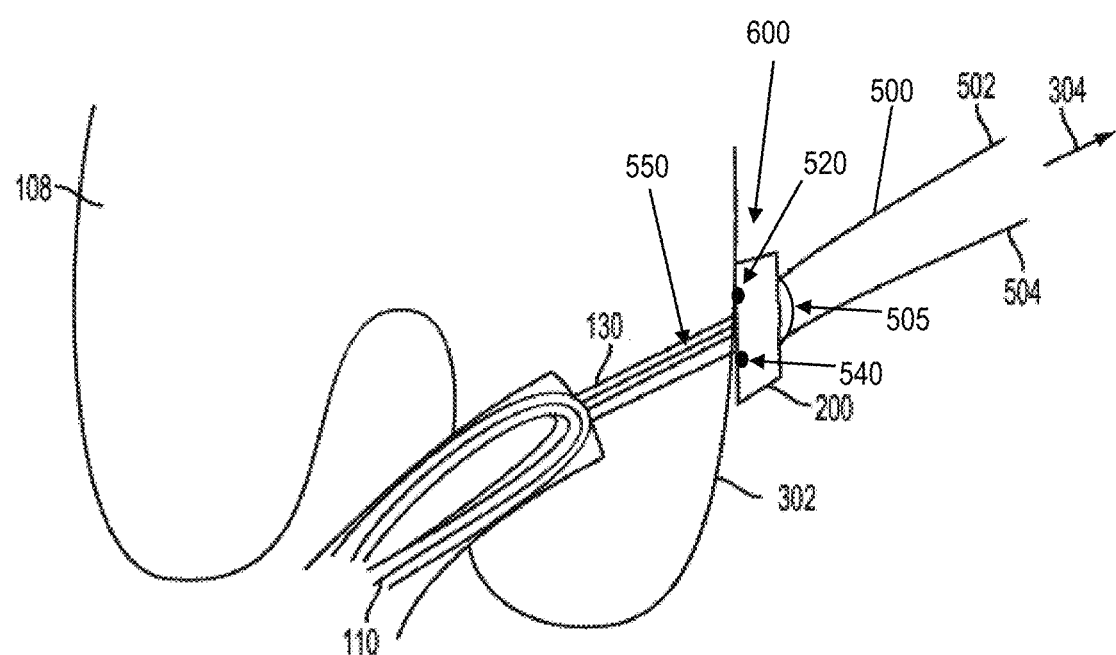
FIG. 11 is a schematic side view of one exemplary embodiment of an adjustable fixation implant disposed in a femur.

The implant 600 provided for in FIG. 11 includes the suture construct 400 and the fixation body 200. The bridge portion 505 that extends between the two knots 520, 540 can be hung across the body 200, which is seated on the far side of the bone 108 once implanted. Each knot 520, 540 has the suture tails 502, 504, respectively, extending from one side of the knot, the tails extending through the button 200, and the filament that forms the loops 501, 503 extending from an opposite side of the knots 520, 540, respectively. The loops 501, 503 form an interlocked loop portion, illustrated at the terminal end 550t (FIG. 2) that results in the one-way adjustable fixation loop 550.

The implant 600 can be prepared by coupling a ligament graft taken from a cadaver or the patient's own tissue, e.g., the soft tissue 110, to the body 200 by way of the one-way adjustable fixation loop 550. The soft tissue 110 is hung over, or otherwise associated with, the one-way adjustable fixation loop 550 and tension can be applied to the suture tails 502, 504 to reduce the size of the opening of the loop 550 until the soft tissue 110 is at a desired location with respect to the bone tunnel 130.

More particularly, after the tunnel 130 is drilled through the bone 108 at the repair site, the implant 600 can be introduced. In some instances, the combination of the suture construct 400 and body 200 may already be coupled together to form the implant 600. In other instances, the suture construct 400 can be associated with one or more bodies 200 in conjunction with performing the repair.

The body 200 can be introduced into the bone tunnel of the patient's tibia 106 and pulled through the tibia and femur 108 until the body 200 emerges on an outer portion of the patient's femur. In order to pull the body 200 through the bone tunnel, a shuttle suture (not shown) can be threaded through the fourth through-hole 218 (see FIG. 3) that is near the first (front) terminal end 202 of the body 200. The shuttle suture can be used to pull the body through the bone tunnel 130 approximately along its longitudinal axis 214 to minimize the cross-sectional area of the body. Pulling the body 200 in this manner can also pull the fixation loop 550 and graft 110 into the patient's body.

After the body 200 emerges from the bone tunnel 130 at an outer surface of the femur 108, the body 200 can be flipped into an orientation that places the second side 208 flush against the outer surface of the femur such that the body 200 cannot reenter the bone tunnel 130. Flipping the orientation of the body 200 can be accomplished by pulling on a rotation suture (not shown) that can be threaded through the fifth through-hole 220 (see FIG. 3) near the second (rear) terminal end 204 of the body 200. It should be noted that both shuttle and rotation sutures can be threaded through the fourth and fifth through-holes 218, 220, or other through-holes if desired, prior to introducing the body 200 into a bone tunnel. After the body 200 has been pulled through the bone tunnel and flipped to sit flush against an outer surface 302 of the femur 108 (as shown in FIG. 11), the shuttle and rotation sutures can be removed by simply pulling on a free end thereof.

As shown in FIG. 11, and similar to described above with respect to FIGS. 10A-10C, the terminal ends 502, 504 can be tensioned in the direction of arrow 304 to reduce the size of the one-way fixation loop 550 and draw the ligament graft 110 into the bone tunnel 130 formed in the femur 108. The size of the fixation loop 550 can be reduced until a desired amount of the graft 110 resides within the bone tunnel 130. Tensioning the terminal ends 502, 504 of the suture length 500 draws suture through the corresponding knot 520, 540 positioned below the body 200. The bridge portion 505 of suture 500 connects the first knot 520 to the second knot 540 such that movement of the body 200 away from the femur 108 is prevented by the tensioning of the bridge portion 505 causing the two knots 520, 540 to lock and secure the body against the femur 108. If desired, additional supplementary fixation (e.g., by way of one or more half hitch knots) can be applied to the tails 502, 504.

To complete the procedure, the terminal ends of the ligament graft 110 can be secured within the bone tunnel 130 formed in the patient's tibia 106 in any of a variety of manners known in the art. In certain embodiments, the terminal ends 502, 504 can be joined together to provide a user with a single suture strand for tensioning. This can be accomplished in a number of manners known in the art. In some embodiments, for example, the terminal ends 502, 504 can be associated together, such as by passing one into a volume of the other, to form a single terminal end. When the desired depth/repair tension is achieved, the suture tails 502, 504 can be trimmed to length. Additional details related to implantation techniques that can be used in conjunction with the present disclosures, including but not limited to details that further expand upon the disclosed techniques and provide alternatives to the described techniques, are provided in U.S. Pat. Nos. 9,974,643 and 9,757,113, the contents of each which is incorporated by reference above.

Figure 12A:
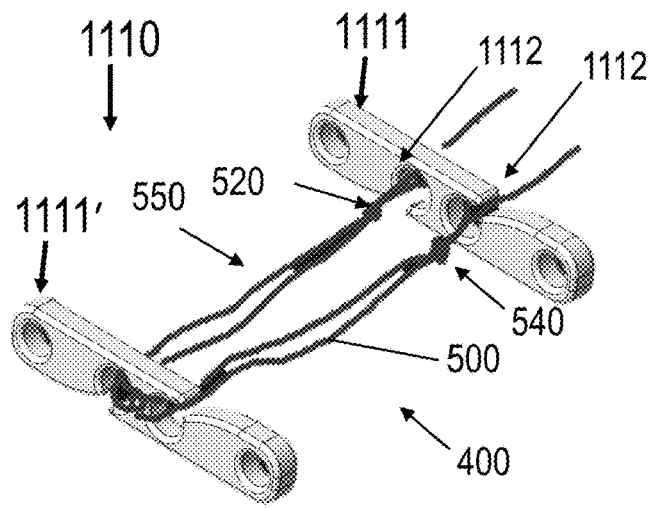
FIG. 12A is a perspective view of the suture construct of FIG. 4A, the suture construct being associated with two fixation bodies.
Figure 12B:
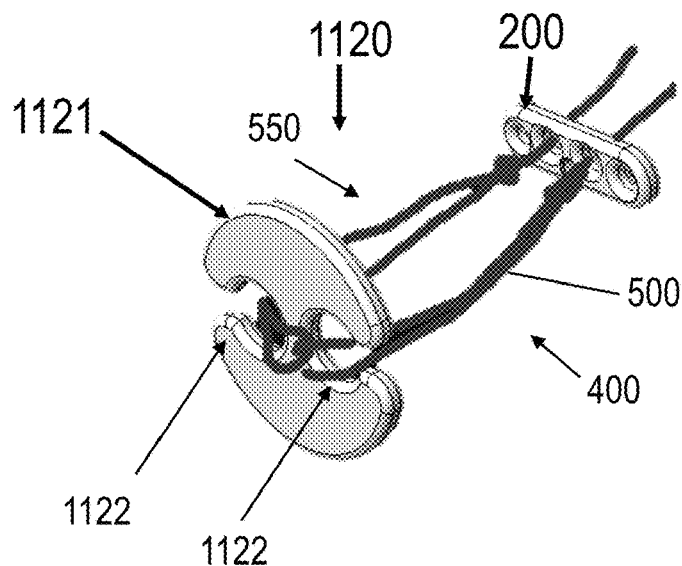
FIG. 12B is a perspective view of the suture construct of FIG. 4A, the suture construct being associated with two fixation bodies.
Figure 12C:
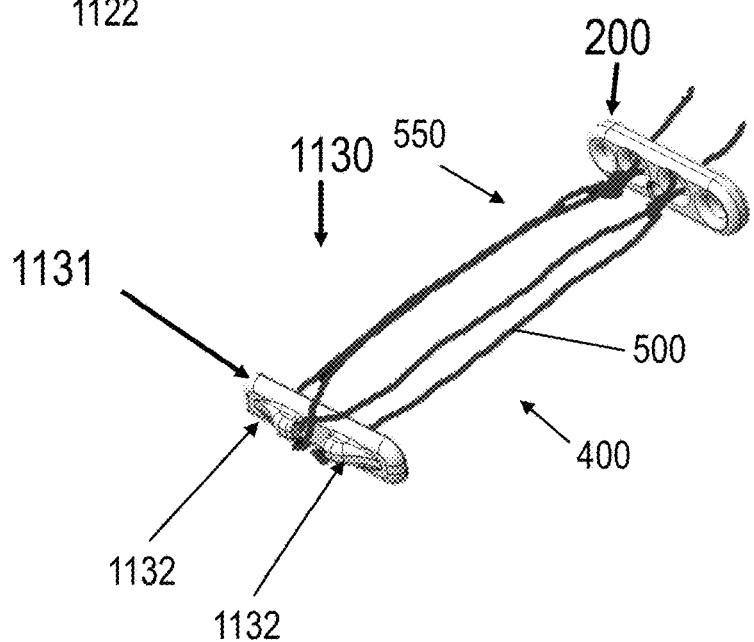
FIG. 12C is a perspective view of the suture construct of FIG. 4A, the suture construct being associated with two fixation bodies.

As discussed above, embodiment of the present disclosure includes the use of two or more fixation bodies. The bodies may be of a closed geometry where the loop is threaded to the buttons when it is assembled (as illustrated in FIG. 5), or an open geometry where the loop is hung over a portion of the button, as shown in FIGS. 12A-12C. A person skilled in the art will further recognize other techniques that can be used to associate the constructs provided for herein with fixation bodies.

FIG. 12A shows an implant 1110 including two open-geometry fixation bodies or buttons 1111, 1111' and the suture 500 arranged with the one-way adjustable fixation loop 550 to form the surgical repair construct 400. The open-geometry buttons 1111, 1111' include gaps 1112 in their though-holes to facilitate the construction of the implant 1110 without threading the suture 500 through closed through-holes. This enables the suture 500 to be tied to form the surgical construct 400 having the one-way adjustable fixation loop 550 in advance of assembling the buttons 1111, 1111' to the suture 500 and/or more easily associating and disassociating the construct 400 from the fixation bodies 1111, 1111'.

FIG. 12B is another embodiment of an implant 1120, in this instance coupling the suture 500 of the surgical construct 400 having the one-way adjustable fixation loop 550 to each of the closed-geometry fixation body or button 200 and another example of an open geometry fixation body or plate 1121. The plate 1121 includes lateral gaps 1120 for coupling the open geometry plate 1121 to the suture 500 after the suture has been threaded though the closed-geometry button 200, as described herein. Again, the open geometry can allow the construct 400 to be more easily associated and disassociated from the fixation body 1121.

FIG. 12C is yet another embodiment of an implant 1130, in this instance coupling the suture 500 of the surgical construct 400 having the one-way adjustable fixation loop 550 to each of the closed-geometry fixation body or button 200 and another example of a closed geometry fixation body or button 1131. The button 1131 includes internal passageways 1132 for threading the suture 500 though the closed geometry button 1131. The internal passageways 1132 can better protect the suture 500 from fraying or other damage during the course of a procedure, and/or once the implant is implanted in the body.

Figure 13:
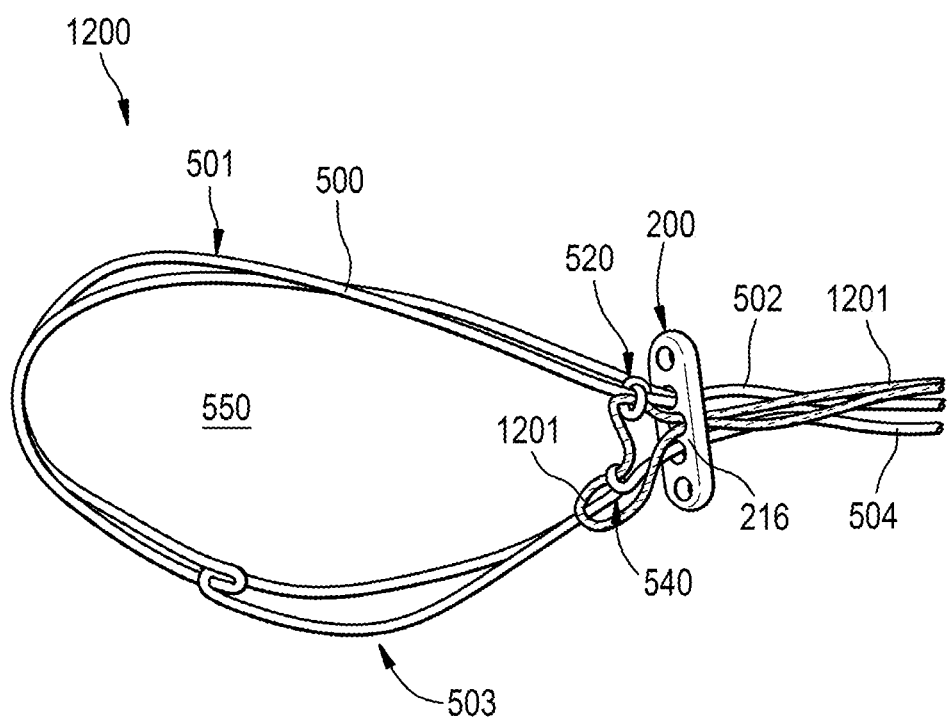
FIG. 13 is a side view of one exemplary embodiment of an adjustable fixation implant that includes the suture construct of FIG. 4A coupled to the fixation body of FIG. 3, the suture construct also including a utility stitch.

FIG. 13 is an illustration of an implant 1200 including the suture 500 forming the one-way adjustable fixation loop 550, the single cortical button 200, and a utility stitch 1201. For applications where over tensioning is a concern and reversing the tension is advantageous (e.g., procedures involving the medial patella femoral ligament), the utility stitch 1201 may be added to the knots 520, 540, for instance by passing or extending limbs of the utility stitch 1201 through the knots 520, 540 such that when tension is applied to the utility stitch 1201, the knots 520, 540 can be open to permit the button 200 to slide, thereby expanding the adjustable fixation loop 550. The utility stitch 1201 can be threaded through one of the through-holes of the body 200, as shown the third through-hole 216, which enables tension applied to the utility stitch 1201 to pull on the body 200 to expand the adjustable fixation loop 550. Due to interference in loops caused by compressive forces at the loop junctions a toggling technique, illustrated in FIGS. 14A-14C, may be employed to prevent the migration of the junction into a compressed region (i.e., where the soft tissue is hung through the loop 550).

Figure 14A:
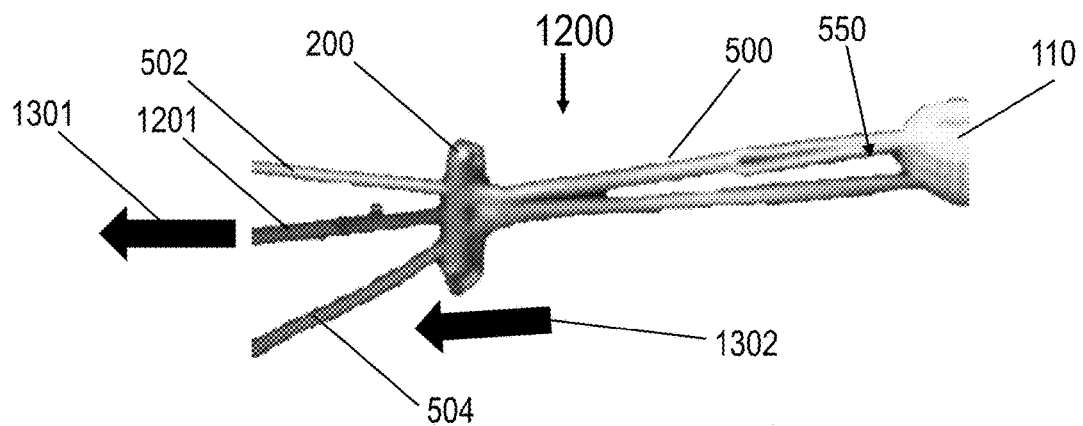
FIGS. 14A-14C are schematic side views of steps of one exemplary embodiment of a method of using the adjustable fixation implant of FIG. 13.
Figure 14B:
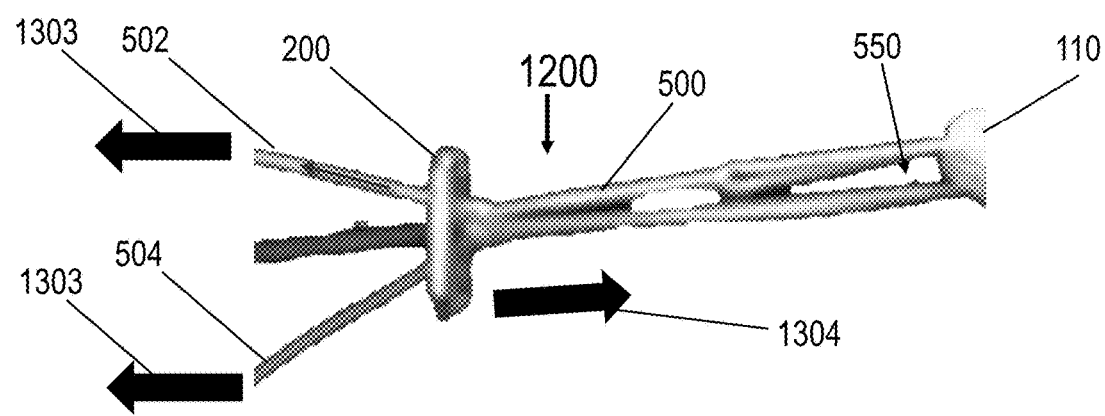
Figure 14C:
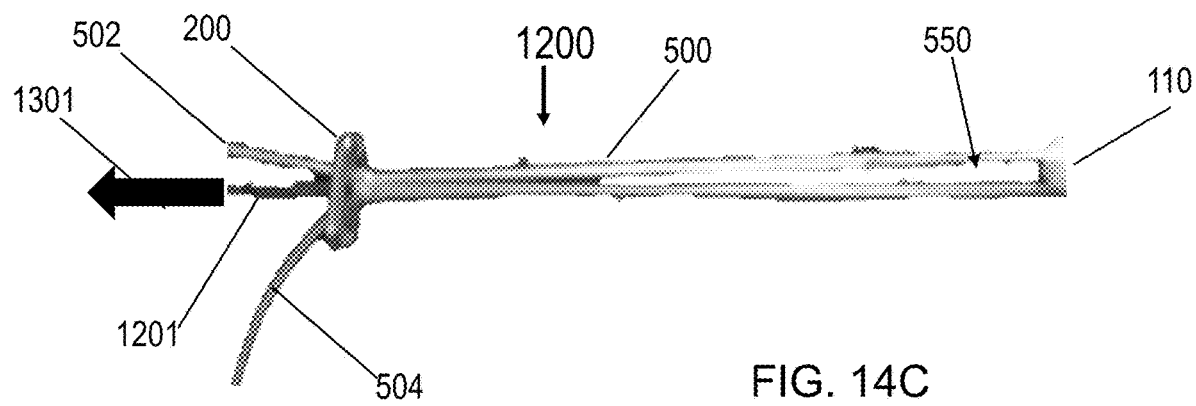

FIG. 14A shows a soft tissue 110 hung on the adjustable fixation loop 550, and force applied, indicated by arrow 1301, to the utility stitch 1201 to relax the knots 520, 540 and expand the adjustable fixation loop 550 by drawing the button 200 away from the soft tissue 110, indicated by arrow 1302. Afterwards, and as shown in FIG. 14B, force applied, indicated by arrows 1303 to the first and second tails 502, 504 can constrict the adjustable fixation loop 550 by drawing the button 200 toward the soft tissue 110, as indicated by arrow 1304. Finally, as shown in FIG. 14C, even after the adjustable fixation loop 550 has been constricted, and the knots 520, 540 locked, force applied to the utility stitch 1201, for instance as indicated by arrow 1301, still can relax the knots 520, 540 and expand the adjustable fixation loop 550 by drawing the button 200 away from the soft tissue 110.

One skilled in the art will appreciate further features and advantages of the disclosure based on the above-described embodiments. Accordingly, the disclosure is not to be limited by what has been particularly shown and described, except as indicated by the appended claims. All publications and references cited herein are expressly incorporated herein by reference in their entirety.

What is claimed is:

1. A suture construct formed from a suture filament, comprising:
   a first knot formed in the suture filament to create a first loop extending from the first knot, the first loop defining a first loop opening;
   a first tail of the suture filament extending from the first knot;
   a bridge portion of the suture filament extending from the first knot;
   a second knot formed in the suture filament to create a second loop extending from the second knot, the second loop defining a second loop opening, and a portion of the suture filament that defines the second loop passing through the first loop opening to define an adjustable loop of the suture construct, the adjustable loop defining an adjustable loop opening; and
   a second tail of the suture filament extending from the second knot,
   wherein the first tail is configured to slide with respect to the first knot to reduce a size of the first loop opening, and thus reduce the size of the adjustable loop opening,
   wherein the second tail is configured to slide with respect to the second knot to reduce a size of the second loop opening, and thus reduce the size of the adjustable loop opening, and
   wherein the bridge portion of the suture filament connects the first knot to the second knot and is configured to prevent expansion of the adjustable loop opening when the suture is manipulated into a locked configuration.

2. The suture construct of claim 1, wherein at least one of the first knot or the second knot comprises a self-locking knot.

3. The suture construct of claim 2, wherein the self-locking knot comprises at least one of a FIG. 8 noose knot or an expanded FIG. 8 noose knot.

4. The suture construct of claim 2, wherein the self-locking knot comprises at least one prusik-style knot.

5. The suture construct of claim 1, wherein the suture filament is unspliced at locations of the first and second knots.

6. The suture construct of claim 1, further comprising a second suture filament configured to capture a portion of the first knot and the second knot, with a first limb of the second suture filament extending to the first knot and a second limb of the second suture filament extending to the second knot such that tension on at least one of the first or second limbs loosens the respective first or second knots.

7. The suture construct of claim 1, further comprising a fixation body coupled to the bridge portion of the suture filament.

8. The suture construct of claim 7, further comprising a second fixation body coupled to the adjustable loop.

9. The suture construct of claim 1, wherein the suture further comprises an unlocked configuration, with the suture being configured to be moved between the unlocked configuration and the locked configuration by adjusting relative loading of at least one of the bridge portion, the first tail, or the second tail.

10. A surgical implant, comprising:
a fixation body having a longitudinal axis extending therealong, first and second sides, and first and second through-holes; and
a suture filament coupled to the fixation body, the suture filament, comprising:
a first portion having a first tail extending through the first through-hole, a first knot formed thereon and disposed on the first side of the body, and a first loop portion extending from the first knot, away from the body;
a second portion having a second tail extending through the second through-hole, a second knot formed thereon and disposed on the first side of the body, and a second loop portion extending from the second knot, away from the body, the second portion passing through an opening of the first loop portion such that the second loop portion is coupled to the first loop portion to define an adjustable loop of the surgical implant; and
a bridge portion extending from the first knot to the second knot,
wherein the first and second knots are configured such that tension on the first tail constricts the adjustable loop by constricting the first loop portion and tension on the second tail constricts the adjustable loop by constricting the second loop portion, and
wherein the first and second knots are further configured such that tension on the bridge portion prevents expansion of the adjustable loop.

11. The surgical implant of claim 10, wherein at least one of the first knot or the second knot comprises a self-locking knot.

12. The surgical implant of claim 10, wherein the suture filament is unspliced at locations of the first and second knots.

13. The surgical implant of claim 10, wherein the fixation body comprises a cortical button.

14. The surgical implant of claim 10, wherein the bridge portion extends from the first knot, through the first through-hole, across the body, and through the second through-hole to the second knot.

15. The suture construct of claim 14, further comprising a second fixation body, the second fixation body being coupled to the adjustable loop.

16. The surgical implant of claim 10,
wherein the surgical implant further comprises a second suture filament that captures a portion of the first knot and the second knot, with a first limb of the second suture filament extending to the first knot, and a second limb of the second suture filament extending to the second knot, and
wherein the second suture filament is configured such that tension on at least one of the first or second limbs loosens the respective first or second knots.

17. A method for preparing a surgical implant, comprising:
forming a first knot in a first portion of a suture length to form a first tail extending from one side of the first knot and a second portion of the suture length extending from an opposite side of the first knot;
forming a first loop from the second portion, the first loop being closed by way of the first knot;
forming a second knot in the second portion of the suture length to form a second tail extending from one side of the second knot and a third portion of the suture length extending from an opposite side of the second knot; and
forming a second loop from the third portion, the second loop being closed by way of the second knot, the second loop being interconnected with the first loop by passing the third portion through an opening of the first loop to define an adjustable fixation loop of the surgical implant.

18. The method of claim 17, wherein the second portion of the suture length comprises a bridge portion that extends between the first knot and the second knot.

19. The method of claim 17, wherein at least one of the first tail or the second tail is configured to constrict a size of an opening defined by the adjustable fixation loop when tension is applied thereto to constrict a size of first or second openings defined by the respective first or second loops.

20. The method of claim 17, further comprising:
passing the first tail through a first through-hole of a fixation body;
passing the second tail through a second through-hole of the fixation body; and
passing the second portion of the suture length through at least two of the first through-hole of the fixation body, the second through-hole of the fixation body, or at least one more through-hole of the fixation body.

21. The method of claim 20, further comprising coupling the adjustable fixation loop to a second fixation body.

* * * * *